United States Patent [19]

Otagiri et al.

[11] 4,360,598
[45] Nov. 23, 1982

[54] ZIRCONIA CERAMICS AND A METHOD OF PRODUCING THE SAME

[75] Inventors: Tadashi Otagiri; Tetsuo Watanabe, both of Nagoya; Syunzo Mase, Tobishima, all of Japan

[73] Assignee: NGK Insulators, Ltd., Nagoya, Japan

[21] Appl. No.: 245,280

[22] Filed: Mar. 19, 1981

[30] Foreign Application Priority Data

Mar. 26, 1980 [JP] Japan ............................. 55-37552
Feb. 17, 1981 [JP] Japan ............................. 56-20833

[51] Int. Cl.$^3$ ............................................ C04B 35/48
[52] U.S. Cl. ............................. 501/103; 64/56; 423/266; 423/608; 501/152
[58] Field of Search ............... 423/266, 608; 264/65, 264/56; 501/103, 152; 204/195 S; 429/193

[56] References Cited

U.S. PATENT DOCUMENTS

| | | | |
|---|---|---|---|
| 3,303,033 | 2/1967 | La Grange et al. | 501/103 |
| 3,334,962 | 8/1967 | Clearfield | 501/103 |
| 3,432,314 | 3/1969 | Mazdiyasni et al | 501/103 |
| 3,514,252 | 5/1970 | Levy | 423/608 |
| 4,219,359 | 8/1980 | Miwa et al. | 501/152 |
| 4,266,979 | 5/1981 | Miyoshi et al. | 501/103 |

FOREIGN PATENT DOCUMENTS

| | | | |
|---|---|---|---|
| 46-18378 | 5/1971 | Japan | 423/608 |
| 54-109898 | 8/1979 | Japan | 501/103 |
| 352841 | 10/1972 | U.S.S.R. | 423/608 |

Primary Examiner—Mark Bell
Attorney, Agent, or Firm—Stevens, Davis, Miller & Mosher

[57] ABSTRACT

Zirconia ceramics consisting mainly of $ZrO_2$ and $Y_2O_3$ in a molar ratio of $Y_2O_3/ZrO_2$ of $2/98 \sim 7/93$ and consisting of crystal grains having a mixed phase consisting essentially of tetragonal phase and cubic phase or having a phase consisting essentially of tetragonal phase, the average size of the crystal grains being not larger than 2 μm, has a high strength and shows little deterioration of strength due to the lapse of time, and is suitable as a solid electrolyte for oxygen concentration cells, machine parts for internal combustion engines, thermistors, cutting tools and other industrial materials.

6 Claims, 4 Drawing Figures

ZIRCONIA CERAMICS AND A METHOD OF PRODUCING THE SAME

BACKGROUND OF THE INVENTION (1) Field of the Invention

The present invention relates to $ZrO_2$—$Y_2O_3$ zirconia ceramics having high strength and high resistance against deterioration of strength due to use for a long period of time within a specifically limited temperature range, and a method for producing the same.

(2) Description of the Prior Art

There have hitherto been known, as $ZrO_2$—$Y_2O_3$ zirconia ceramics, fully stabilized zirconia ceramics consisting only of cubic phase and partially stabilized zirconia ceramics consisting of cubic phase and monoclinic phase, both of which are used as a heat resistant material and a solid electrolyte and the like. The fully stabilized zirconia ceramics are stable within a temperature range of from room temperature to about 1,500° C. and show very little deterioration of strength due to use for a long period of time. However, the fully stabilized zirconia ceramics are poor in strength, and, for example, are apt to be very easily broken due to thermal shock during use as a solid electrolyte for an oxygen sensor used for detecting oxygen concentration in the exhaust gas of automobiles and the like. The partially stabilized zirconia ceramics consisting of cubic phase and monoclinic phase are higher in strength and thermal shock resistance than the fully stabilized zirconia ceramics. However, they have such serious drawbacks that the partially stabilized zirconia ceramics deteriorate very noticeably in their strength due to the lapse of time within a specifically limited temperature range of from 200° C. to 300° C. When such zirconia ceramics are used for a long period of time at a temperature within the above described temperature range, a large number of fine cracks are formed on the surface of the ceramics to make the ceramics water absorptive and to deteriorate their strength, resulting in breakage of the ceramics.

The reason for breakage of the partially stabilized zirconia ceramics may be as follows. Although the partially stabilized $ZrO_2$—$Y_2O_3$ zirconia ceramics consist of cubic phase and monoclinic phase at room temperature, they consist of cubic phase and tetragonal phase at the firing temperature of about 1,500° C. Therefore, the crystal grains of tetragonal phase at the firing temperature change their crystal phase from tetragonal phase into monoclinic phase at about 500° C. during the cooling from about 1,500° C. to room temperature, and excess stress is caused due to the volume change caused by the phase transformation. Thus a large number of fine cracks are formed in the crystal grains and grow up therein during use for a long period of time at a temperature within the range of from 200° C. to 300° C., resulting in breakage of the ceramics. Furthermore, when the partially stabilized zirconia ceramics consisting of cubic phase and monoclinic phase are repeatedly heated and cooled between room temperature and about 800° C., the ceramics exhibit different thermal expansion curves in the heating direction and cooling direction due to the phase transformation between the monoclinic phase and tetragonal phase caused at about 500° C., that is, exhibit a so-called hysteresis curve. Moreover when the ceramics are heated from room temperature and then cooled to the original room temperature, the ceramics have different dimensions before and after the heating, and therefore the ceramics can not maintain accurate dimensions.

SUMMARY OF THE INVENTION

An object of the present invention is to provide a zirconia ceramics which is free from the above described drawbacks of the conventional partially stabilized zirconia ceramics, has a high strength and a remarkably improved resistance against deterioration of strength due to the lapse of time within a specifically limited temperature range of from 200° C. to 300° C., is free from the hysteresis phenomenon due to the phase transformation in the thermal expansion curve from room temperature to about 800° C., and further can maintain a high dimensional accuracy at room temperature.

Another object of the present invention is to provide a method of producing the above described zirconia ceramics.

That is, a feature of the present invention is the provision of zirconia ceramics consisting essentially of $ZrO_2$ and $Y_2O_3$ in a molar ratio of $Y_2O_3/ZrO_2$ of $2/98 \sim 7/93$, and consisting of crystal grains having a mixed phase consisting essentially of tetragonal phase and cubic phase or having a phase consisting essentially of tetragonal phase, the average size of said crystal grains being not larger than 2 $\mu$m.

Another feature of the present invention is the provision of a method of producing zirconia ceramics consisting of crystal grains having a mixed phase consisting essentially of tetragonal phase and cubic phase or having a phase consisting essentially of tetragonal phase, the average size of said crystal grains being not larger than 2 $\mu$m, comprising mixing zirconium oxide having a crystallite size of not larger than 1,000 Å or amorphous zirconium oxide with an yttrium compound in a mixing ratio, calculated as oxide, of $Y_2O_3/ZrO_2$ of $2/98 \sim 7/93$, molding the mixture into a molded article, and firing the molded article at a temperature within the range of $1,000° \sim 1,550°$ C.

In the specification, the term "zirconia ceramics consisting of crystal grains having a mixed phase consisting essentially of tetragonal phase and cubic phase" may be merely referred to as "zirconia ceramics having a mixed crystal phase consisting essentially of tetragonal phase and cubic phase"; and the term "zirconia ceramics consisting of crystal grains having a phase consisting essentially of tetragonal phase" may be merely referred to as "zirconia ceramics having a crystal phase consisting essentially of tetragonal phase".

The present invention is based on the discoveries that, when crystal grains constituting $ZrO_2$—$Y_2O_3$ zirconia ceramics have an average grain size of not larger than a specifically limited value, the tetragonal phase, which is not stable at a temperature of not higher than about 500° C. due to the phase transformation at about 500° C., can be stably maintained within the temperature range of from 500° C. to room temperature without causing phase transformation from tetragonal phase into monoclinic phase; that is, when the crystal grains constituting the zirconia ceramics have a mixed phase consisting essentially of cubic phase and tetragonal phase or have a phase consisting essentially of tetragonal phase, the zirconia ceramics have very high strength, show very little deterioration of strength due to the lapse of time at a temperature within a specifically limited temperature range and are free from dimensional change due to heating and cooling within the temperature range of from room temperature to 800° C. Further, in the production of the above described zirconia ceramics, it is a most important factor that a molded article to be fired into the zirconia ceramics according to the present invention is constituted with zirconium oxide having a crystallite size of not larger than the specifically limited size or with amorphous zirconium oxide, and further it is necessary that the amount of stabilizer and the firing temperature are within a specifically limited range.

DESCRIPTION OF THE PREFERRED EMBODIMENT

The present invention will hereinafter be explained in more detail.

It has been found that, in order to keep stably the crystal phase of zirconia ceramics to tetragonal phase, it is very important that the zirconia ceramics consist of crystal grains having an average grain size of not larger than 2 μm, preferably not larger than 1 μm.

Figure 1:
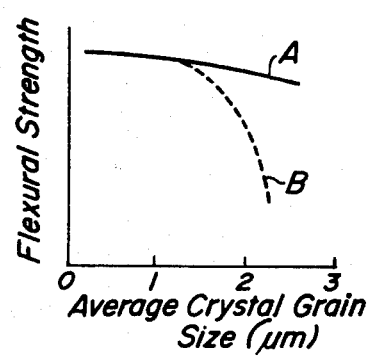
FIG. 1 is a graph illustrating a relation between the average crystal grain size of zirconia ceramics and the flexural strength thereof before and after a durability test.

That is, it has been found from an investigation of the relation between the average crystal grain size and the flexural strength of zirconia ceramics by the use of zirconia ceramics of the present invention and conventional zirconia ceramics that, in zirconia ceramics before a durability test, the strength of the ceramics does not noticeably decrease even when the average crystal grain size becomes larger than 2 μm as illustrated in curve A in FIG. 1. However, in zirconia ceramics after a durability test, wherein the ceramics are maintained for 1,500 hours within a specifically limited temperature range of 200°~300° C., when the average crystal grain size becomes larger than 2 μm the strength of the ceramics is noticeably decreased as illustrated by curve B in FIG. 1 due to the presence of fine cracks formed therein due to the formation of excess monoclinic phase.

FIG. 1 shows the variation rate of flexural strength of zirconia ceramics before and after the durability test depending upon the average crystal grain size at a specifically limited molar ratio of $Y_2O_3/ZrO_2$. In zirconia ceramics having different molar ratios of $Y_2O_3/ZrO_2$, even when the ceramics have the same crystal grain size, they have different strengths. The measuring method of the strength in the above described experiment is the same as that described in the following example 1.

The reason why transformation from tetragonal phase to monoclinic phase hardly occurs in the case where the crystal grain size is small may be that, when crystal grains have a very fine size, the tetragonal phase is stabler than the monoclinic phase due to the surface free energy of the grains. The fact that the tetragonal phase is stably present within a wide range from room temperature to high temperature contributes highly to the improvement of the strength of zirconia ceramics and to the prevention of deterioration of strength due to the lapse of time. As a result, hysteresis due to phase transformation does not occur in the thermal expansion curve in repeated heatings and coolings.

The measurement of average crystal grain size is carried out in the following manner. The mirror-polished surface of a ceramics is etched with hydrofluoric acid, the number n of grains contained in a certain area S containing at least 50 grains is counted by an electron photomicrograph, and the diameter d of a circle having an area equal to the average area s per one grain is calculated by the formula $d=(4s/\pi)^{\frac{1}{2}}$. The value of d is calculated in at least 3 fields for one sample and the average value is used as the average crystal grain size. The number n of grains is the total sum of the number of grains contained completely in the certain area S and $\frac{1}{2}$ of the number of grains lying on the boundary line defining the certain area S.

Figure 2:
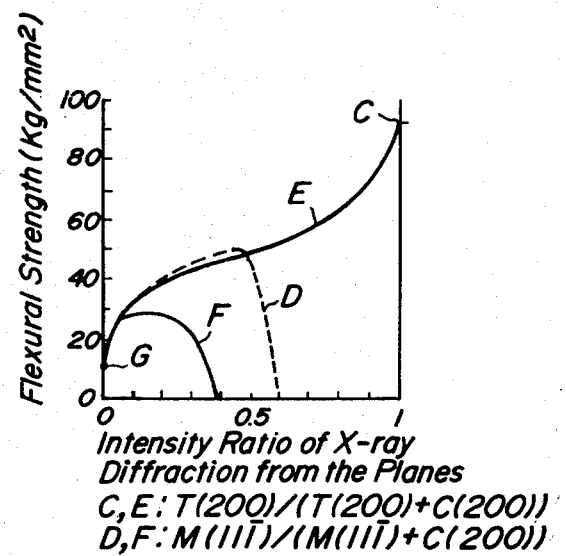
FIG. 2 is a graph illustrating a relation between the intensity ratio of the X-ray diffraction from the plane (200) of cubic phase to the X-ray diffraction from the plane (200) of tetragonal phase in zirconia ceramics and the flexural strength of the ceramics, and further a relation between the intensity ratio of the X-ray diffraction from the plane (200) of cubic phase to the X-ray diffraction from the plane ($11\bar{1}$) of monoclinic phase in zirconia ceramics and the flexural strength of the ceramics before and after deterioration due to the lapse of time.

A relation between the intensity ratio of X-ray diffraction from the planes in zirconia ceramics and the flexural strength of the ceramics is shown in FIG. 2. When the intensities of X-ray diffraction from the plane (200) of tetragonal phase, from the plane ($11\bar{1}$) of monoclinic phase and from the plane (200) of cubic phase are represented by T(200), M($11\bar{1}$) and C(200) respectively, the flexural strength of the zirconia ceramics C having a crystal phase consisting essentially of tetragonal phase according to the present invention is higher than the flexural strength D, before deterioration, of conventional zirconia ceramics consisting of cubic phase and monoclinic phase. Further, the flexural strength of zirconia ceramics E having a mixed crystal phase consisting essentially of cubic phase and tetragonal phase according to the present invention is higher than the flexural strength F, after deterioration due to the lapse of time at a temperature within a specifically limited range, of zirconia ceramics consisting of cubic phase and monoclinic phase. Further, the zirconia ceramics C and E according to the present invention are of higher strength than the zirconia ceramics G having a crystal phase consisting only of cubic phase, and their strength is increased corresponding to the increase of the content of tetragonal phase.

The term "zirconia ceramics having a mixed crystal phase consisting essentially of cubic phase and tetragonal phase" used in this specification means not only zirconia ceramics having a mixed crystal phase consisting only of cubic phase and tetragonal phase, but also zirconia ceramics having a mixed crystal phase consisting essentially of cubic phase and tetragonal phase and containing monoclinic phase in an amount defined by a condition that the intensity ratio of T(200)/(T(200)+C(200)) is at least 0.05, the intensity ratio of M($11\bar{1}$)/T(200) is not more than 1.0 and the intensity ratio of M($11\bar{1}$)/(T(200)+C(200)) is not more than 0.4. The range of monoclinic phase defined by the above described intensity ratios of X-ray diffractions at the peak corresponds to not larger than about 20% by volume of monoclinic phase based on the total crystal phase. Further, the term "zirconia ceramics having a crystal phase consisting essentially of tetragonal phase"

used in this specification means not only zirconia ceramics having a crystal phase consisting only of tetragonal phase, but also zirconia ceramics having a crystal phase consisting essentially of tetragonal phase and containing at least one of monoclinic phase and cubic phase in an amount defined by a condition that the intensity ratio of $(M(11\bar{1})+C(200))/T(200)$ of the X-ray diffraction from the planes is not more than 0.4. The above described range of the intensity ratio of the X-ray diffractions from the planes corresponds to not more than 20% by volume of the content of at least one of monoclinic phase and cubic phase.

Further, the term "zirconia ceramics consisting mainly of $ZrO_2$ and $Y_2O_3$" used in the present invention means zirconia ceramics, in which $Y_2O_3$ is mainly used as a stabilizer for $ZrO_2$. Not more than about 30 mol% of the $Y_2O_3$ may be replaced by oxides of rare earth elements, such as $Yb_2O_3$, $Sc_2O_3$, $Nb_2O_3$, $Sm_2O_3$ and the like; CaO or MgO. The zirconia ceramics of the present invention may contain not more than 30% by weight, based on the total amount of the ceramics, of sintering aids, such as $SiO_2$, $Al_2O_3$, clay and the like. In the identification of the crystal phase constituting ceramics, the surface of the ceramics is polished to form a mirror surface, and the crystal phase of the mirror surface is identified by means of the X-ray diffractiometry.

When the zirconia ceramics having a mixed crystal phase consisting essentially of cubic phase and tetragonal phase or the zirconia ceramics having a crystal phase consisting essentially of tetragonal phase according to the present invention are used in the production of oxygen concentration cells, all the resulting oxygen concentration cells exhibit an electromotive force equal to the theoretical value. Therefore, the zirconia ceramics of the present invention can be satisfactorily used as an oxygen ion-conductive solid electrolyte, too.

In the production of the above described zirconia ceramics of the present invention, zirconium oxide constituting a molded article to be fired into the ceramics is zirconium oxide having a crystallite size of not larger than 1,000 Å or amorphous zirconium oxide, and is preferably zirconium oxide having a crystallite size of 300° ~ 700° Å.

Figure 3:
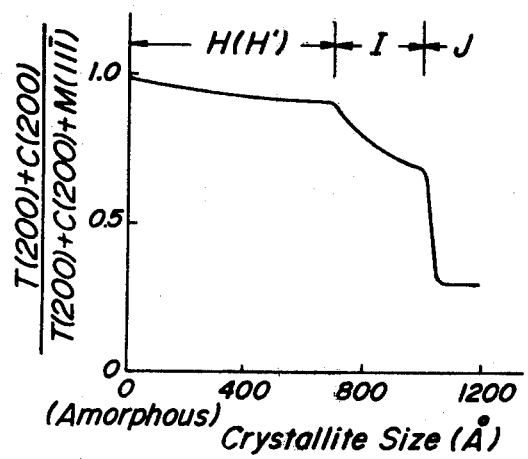
FIGS. 3 and 4 are graphs illustrating a relation between the crystallite size of zirconium oxide and the crystal phase of the ceramics produced therefrom.
Figure 4:
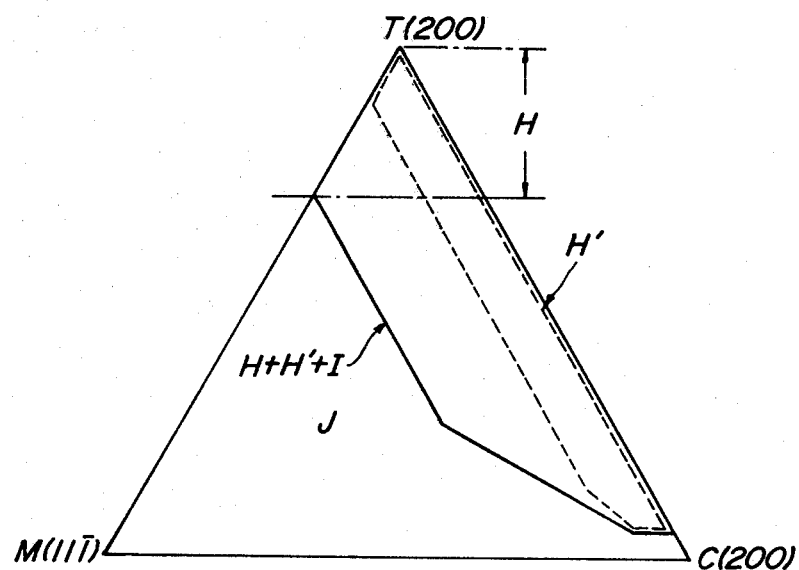

That is, when a relation between the crystallite size of zirconium oxide constituting the molded article and the crystal phase of the resulting zirconia ceramics is represented by a relation between the crystallite size and the intensity ratio of X-ray diffractions, zirconium oxide having a crystallite size of not larger than 700 Å or amorphous zirconium oxide gives a crystal phase (H-region) consisting essentially of tetragonal phase or a mixed crystal phase (H'-region) consisting essentially of cubic phase and tetragonal phase to the resulting zirconia ceramics; zirconium oxide having a crystallite size of 700 ~ 1,000 Å gives a crystal phase (I-region), which is a mixture of the above described tetragonal phase or cubic phase and tetragonal phase with a small amount of monoclinic phase incorporated therein; but zirconium oxide having a crystallite size of larger than 1,000 Å gives a crystal phase (J-region) containing a large amount of monoclinic phase as illustrated in FIGS. 3 and 4.

Zirconium oxide having a crystallite size of 0 μm represents amorphous zirconium oxide. The use of amorphous zirconium oxide causes excessively large firing shrinkage, and therefore crystalline zirconium oxide is preferably used. Accordingly, it is clear from FIGS. 3 and 4 that zirconium oxide constituting the molded article must be zirconium oxide having a crystallite size of not larger than 1,000 Å or amorphous zirconium oxide in order to maintain stably the crystal phase of the resulting zirconia ceramics as a mixed phase consisting essentially of cubic phase and tetragonal phase or as a phase consisting essentially of tetragonal phase, both of which phases show little deterioration of strength due to the lapse of time.

Zirconium oxide having a crystallite size of not larger than 1,000 Å or amorphous zirconium oxide can be obtained by the thermal decomposition of zirconium chloride, zirconium nitrate and the like. However, zirconium oxide powder produced by the thermal decomposition of zirconyl hydroxide ($ZrO(OH)_2 \cdot nH_2O$) at a temperature of 200° ~ 1,100° C., preferably 500° ~ 1,050° C., is advantageously used in the present invention. In this case, when the thermal decomposition temperature of zirconyl hydroxide is lower than 200° C., water contained in the zirconyl hydroxide can not be completely removed, while when the temperature exceeds 1,100° C., the resulting zirconium oxide has a crystallite size of larger than 1,000 Å. Therefore, thermal decomposition temperature lower than 200° C. or higher than 1,100° C. is not preferable.

In the method of producing zirconia ceramics according to the present invention, zirconium oxide is first mixed with an yttrium compound in a mixing ratio of $Y_2O_3/ZrO_2$ (molar ratio) of 2/98 ~ 7/93. In this case, it is very important in order to give a high resistance against deterioration of strength due to the lapse of time to the resulting zirconia ceramics that the mixing ratio of zirconium oxide and an yttrium compound is within the range of 2/98 ~ 7/93 calculated as the molar ratio of $Y_2O_3/ZrO_2$. The reason is as follows. When the molar ratio of $Y_2O_3/ZrO_2$ is less than 2/98, the tetragonal phase which is effective for preventing deterioration due to lapse of time is hardly formed. When the molar ratio exceeds 7/93, the tetragonal phase is not substantially formed, but cubic phase zirconia ceramics are formed. When the molar ratio of $Y_2O_3/ZrO_2$ is within the range of 2/98 ~ 4/96, a mixed crystal phase consisting essentially of cubic phase and tetragonal phase or a crystal phase consisting essentially of tetragonal phase is formed depending upon the combination of the crystallite size of zirconium oxide with the firing condition and other conditions. As the yttrium compound, there can be preferably used yttrium oxide, yttrium chloride, yttrium nitrate, yttrium oxalate and the like.

The mixture of zirconium oxide and an yttrium compound is molded into a molded article having a given shape through a rubber press, extrusion, casting or the like, and the molded article is fired in air at a temperature within the range of 1,000° ~ 1,550° C., preferably within the range of 1,100° ~ 1,450° C., in which the highest temperature is kept for 1 ~ 20 hours. In general, when the firing temperature is lower, a longer firing time is more preferable. When the firing temperature is lower than 1,000° C. or higher than 1,550° C., a large amount of monoclinic phase is formed, and such firing temperature is not preferable. When firing is carried out within the temperature range of 1,000° ~ 1,550° C., a mixed crystal phase consisting essentially of cubic phase and tetragonal phase or a crystal phase consisting essentially of tetragonal phase is stably formed.

When a mixture of zirconium oxide powder and an yttrium compound is heated at a temperature of 200° ~ 1,200° C. for about 1 ~ 10 hours to decompose thermally the yttrium compound, and the thermally decomposed mixture is pulverized in a ball mill or the like, a homogeneous mixture of zirconium oxide and yttrium oxide can be obtained. When the mixture is molded, and the molded article is fired, a dense ceramics can be obtained. Therefore, the pulverized mixture in a ball mill or the like is advantageously used as a raw material. The particle size of the raw material after pulverizing in a ball mill or the like is about 1.0~10 μm.

The crystallite size of zirconium oxide to be used in the present invention is measured by using CuKα radiation by means of X-ray diffractiometry, and calculated by the formula:

$$D = 0.89\lambda/(B-b) \cos \theta$$

In the formula:

D is the crystallite size of zirconium oxide,

λ is 1.541 Å, which is the wavelength of CuKα radiation,

B is a larger value among the half-value width (radian) of the line profile from the plane (11$\bar{1}$) of monoclinic phase and that of the line profile from the plane (111) of tetragonal phase of zirconium oxide, b is the half-value width (radian) of line profile from the plane (101) of α-quartz having a crystallite size of at least 3,000 Å, which is added as an internal standard, and θ is ½ the value of the diffraction angle 2θ of X-ray used in the measurement of the half-value width of zirconium oxide.

The following examples are given for the purpose of illustration of this invention and are not intended as limitations thereof.

EXAMPLE 1

ZrO$_2$ and Y$_2$O$_3$ or their compounds were mixed in a mixing ratio shown in the following Table 1, and the resulting mixture was homogeneously mixed in a ball mill. Then, the mixture was thermally decomposed at 800° C., pulverized in wet state in a ball mill and then dried. The dried powder was press molded, and the molded article was fired at a temperature within the range of from 1,000° C. to 1,400° C. for a period of time of from 1 hour to 3 hours to obtain zirconia ceramics according to the present invention. The average crystal grain size, the intensity ratio of X-ray diffraction, the flexural strength and the volume resistivity of the resulting zirconia ceramics were measured. The intensity ratio of X-ray diffraction was expressed by the ratio of heights of X-ray diffraction from the plane (200) of cubic phase, from the plane (200) of tetragonal phase and from the plane (11$\bar{1}$) of monoclinic phase. The flexural strength was measured by the three-point bending method with respect to rod-shaped ceramics samples of 3.5×3.5×50 mm prepared from the resulting zirconia ceramics. The volume resistivity was measured at 400° C. in the air by the four-terminal method.

The results of the measurements with respect to the resulting zirconia ceramics having various compositions are shown in Table 1. The results of the measurement with respect to zirconia ceramics outside the scope of the present invention are also shown in Table 1 as a comparative sample (Nos. 19~23).

TABLE 1(a)-1

| No. | Molar ratio of stabilizer/ZrO$_2$ calculated as oxide | Composition of stabilizer | Kind of sintering aid | (1) Addition amount of sintering aid (wt %) | (2) Main crystal phase | (3) $\dfrac{T(200)}{T(200) + C(200)}$ | (4) $\dfrac{M(11\bar{1}) + C(200)}{T(200)}$ |
|---|---|---|---|---|---|---|---|
| 1 | 2/98 | Y$_2$O$_3$ | not added | 0 | T | 1 | 0.05 |
| 2 | 2/98 | " | clay | 10 | T | 1 | 0.32 |
| 3 | 3/97 | " | not added | 0 | T | 1 | 0 |
| 4 | 3/97 | " | not added | 0 | T | 0.88 | 0.16 |
| 5 | 3/97 | Y$_2$O$_3$ 75 mol % Yb$_2$O$_3$ 25 mol % | not added | 0 | T | 0.76 | 0.38 |
| 6 | 3.5/96.5 | Y$_2$O$_3$ | alumina | 5 | T | 0.84 | 0.34 |
| 7 | 4/96 | " | not added | 0 | T | 0.75 | 0.37 |
| 8 | 3/97 | " | alumina | 5 | T + C | 0.78 | 0.47 |
| 9 | 4/96 | " | not added | 0 | T + C | 0.68 | 0.54 |
| 10 | 4/96 | Y$_2$O$_3$ 90 mol % CaO 10 mol % | not added | 0 | T + C | 0.62 | 0.79 |
| 11 | 4/96 | Y$_2$O$_3$ | clay | 10 | T + C | 0.67 | 1.0 |
| 12 | 4.5/95.5 | " | not added | 0 | T + C | 0.56 | 0.86 |
| 13 | 5/95 | " | clay | 10 | C + T | 0.40 | 2.3 |
| 14 | 5/95 | " | alumina | 20 | C + T | 0.32 | 2.9 |
| 15 | 5/95 | " | not added | 0 | C + T | 0.30 | 2.3 |
| 16 | 6/94 | " | alumina | 5 | C + T | 0.20 | 4.6 |

Note:
(1) Wt. % of sintering aid based on the total weight of ceramics
(2) T: tetragonal phase, C: cubic phase, M: monoclinic phase
(3) C(200): intensity of X-ray diffraction from the plane (200) of cubic phase
T(200): intensity of X-ray diffraction from the plane (200) of tetragonal phase
(4) M(11$\bar{1}$): intensity of X-ray diffraction from the plane (11$\bar{1}$) of monoclinic phase TABLE 1(a)-2

| No. | $\dfrac{M(11\bar{1})}{T(200)}$ | $\dfrac{M(11\bar{1})}{T(200) + C(200)}$ | Average crystal grain size (μm) | Flexural strength (kg/mm$^2$) | (5) Flexural strength after durability test (kg/mm$^2$) | Volume resistivity (KΩ · cm) |
|---|---|---|---|---|---|---|
| 1 | 0.05 | 0.05 | 0.2 | 97 | 94 | 98 |
| 2 | 0.32 | 0.32 | 1.8 | 108 | 87 | 109 |
| 3 | 0 | 0 | 0.2 | 112 | 110 | 91 |

TABLE 1(a)-2-continued

| No. | $\dfrac{M(11\bar{1})}{T(200)}$ | $\dfrac{M(11\bar{1})}{T(200) + C(200)}$ | Average crystal grain size (μm) | Flexural strength (kg/mm²) | (5) Flexural strength after durability test (kg/mm²) | Volume resistivity (KΩ · cm) |
|---|---|---|---|---|---|---|
| 4 | 0.02 | 0.02 | 0.3 | 76 | 75 | 80 |
| 5 | 0.06 | 0.05 | 0.5 | 59 | 57 | 90 |
| 6 | 0.15 | 0.12 | 1.0 | 65 | 66 | 92 |
| 7 | 0.03 | 0.02 | 0.4 | 58 | 59 | 84 |
| 8 | 0.19 | 0.15 | 1.0 | 60 | 58 | 97 |
| 9 | 0.08 | 0.05 | 0.4 | 55 | 53 | 73 |
| 10 | 0.16 | 0.10 | 0.5 | 51 | 49 | 82 |
| 11 | 0.50 | 0.33 | 1.8 | 53 | 46 | 92 |
| 12 | 0.06 | 0.03 | 0.4 | 49 | 47 | 66 |
| 13 | 0.83 | 0.33 | 1.8 | 46 | 37 | 57 |
| 14 | 0.69 | 0.22 | 1.6 | 44 | 36 | 132 |
| 15 | 0.06 | 0.02 | 0.3 | 41 | 40 | 67 |
| 16 | 0.67 | 0.15 | 1.0 | 36 | 34 | 46 |

Note:
(5) Flexural strength after repeating heating and cooling between 200° C. and 300° C. at temperature raising and lowering rates of 10° C./min for 1,500 hours.

TABLE 1(b)-1

| No. | Molar ratio of stabilizer/ZrO₂ calculated as oxide | Composition of stabilizer | Kind of sintering aid | (1) Addition amount of sintering aid (wt %) | (2) Main crystal phase | (3) $\dfrac{T(200)}{T(200) + C(200)}$ | (4) $\dfrac{M(11\bar{1}) + C(200)}{T(200)}$ |
|---|---|---|---|---|---|---|---|
| 17 | 6/94 | Y₂O₃ | not added | 0 | C + T | 0.09 | 10 |
| 18 | 7/93 | " | not added | 0 | C + T | 0.05 | 18 |
| 19 | 1.5/98.5 | " | not added | 0 | M | M alone | M alone |
| 20 | 8/92 | " | not added | 0 | C | C alone | C alone |
| 21 | 3/97 | " | clay | 10 | T + C + M | 0.68 | 1.4 |
| 22 | 2/98 | " | clay | 10 | T + M | 1 | 2.5 |
| 23 | 5/95 | " | clay | 5 | C + M | 0 | T is absent |

Note:
(1) Wt. % of sintering aid based on the total weight of ceramics
(2) T: tetragonal phase, C: cubic phase, M: monoclinic phase
(3) C(200): intensity of X-ray diffraction from the plane (200) of cubic phase
T(200): intensity of X-ray diffraction from the plane (200) of tetragonal phase
(4) M(11$\bar{1}$): intensity of X-ray diffraction from the plane (11$\bar{1}$) of monoclinic phase TABLE 1(b)-2

| No. | $\dfrac{M(11\bar{1})}{T(200)}$ | $\dfrac{M(11\bar{1})}{T(200) + C(200)}$ | Average crystal grain size (μm) | Flexural strength (kg/mm²) | (5) Flexural strength after durability test (kg/mm²) | Volume resistivity (KΩ · cm) |
|---|---|---|---|---|---|---|
| 17 | 0.15 | 0.01 | 0.4 | 32 | 32 | 58 |
| 18 | 0.4 | 0.02 | 0.4 | 27 | 28 | 42 |
| 19 | M alone | M alone | 0.3 | <1 | broken | measurement is impossible |
| 20 | C alone | C alone | 0.5 | 13 | 14 | 21 |
| 21 | 0.89 | 0.60 | 3.0 | 51 | broken | 103 |
| 22 | 2.5 | 2.5 | 3.0 | 56 | broken | 110 |
| 23 | T is absent | 0.48 | 10 | 50 | broken | 88 |

Note:
(5) Flexural strength after repeating heating and cooling between 200° C. and 300° C. at temperature raising and lowering rates of 10° C./min for 1,500 hours.

EXAMPLE 2

Zirconium oxide and an yttrium compound were mixed in a ball mill in a mixing ratio shown in the following Table 2. The resulting mixture was, directly or after thermal decomposition under the condition described in Table 2, pulverized in a wet state together with a sintering aid in a ball mill and then dried. The dried mixture was press molded, and the molded article was fired at a temperature shown in Table 2 to obtain ceramics. The average crystal grain size of the resulting ceramics, the intensity ratio of tetragonal phase, cubic phase and monoclinic phase in the ceramics and the flexural strength of the ceramics were measured in the same manner as described in Example 1. The crystallite size of zirconium oxide was measured by the use of a mixture to be molded into a molded article. In Table 2 also, zirconia ceramics outside the scope of the present invention are shown as a comparative sample (Nos. 24~28).

TABLE 2(a)-1

| No. | Crystallite size of zirconium oxide (Å) | | Molar ratio of stabilizer/ZrO$_2$ calculated as oxide | Kind of stabilizer indicated by oxide | Kind of stabilizer | Kind of sintering aid | (3) Addition amount of sintering aid (wt %) |
|---|---|---|---|---|---|---|---|
| 1 | 215 | | 2/98 | Y$_2$O$_3$ | Y$_2$O$_3$ | alumina | 5 |
| 2 | 320 | (1) | 2/98 | " | YCl$_3$ | not added | 0 |
| 3 | 350 | (1) | 3/97 | " | Y$_2$O$_3$ | clay | 10 |
| 4 | 430 | (1) | 3/97 | " | YCl$_3$ | not added | 0 |
| 5 | 80 | (1) | 4/96 | " | Y$_2$O$_3$ | not added | 0 |
| 6 | 215 | | 4/96 | " | YCl$_3$ | not added | 0 |
| 7 | 420 | (1) | 4/96 | Y$_2$O$_3$ 90 mol % Yb$_2$O$_3$ 10 mol % | Y$_2$O$_3$ Yb$_2$O$_3$ | not added | 0 |
| 8 | 680 | | 4/96 | Y$_2$O$_3$ | Y(NO$_3$)$_3$ | not added | 0 |
| 9 | 730 | | 4/96 | " | YCl$_3$ | alumina | 5 |
| 10 | 970 | (1) | 4/96 | " | YCl$_3$ | clay | 5 |
| 11 | 320 | (1) | 5/95 | " | Y(NO$_3$)$_3$ | not added | 0 |
| 12 | 420 | (1) | 5/95 | " | Y$_2$(C$_2$O$_4$)$_3$ | clay | 20 |
| 13 | 550 | | 5/95 | " | Y$_2$O$_3$ | silica | 5 |
| 14 | 460 | (1) | 5/95 | Y$_2$O$_3$ 80 mol % CaO 20 mol % | Y$_2$O$_3$ CaO | alumina | 5 |
| 15 | 350 | (1) | 5/95 | Y$_2$O$_3$ | Y$_2$O$_3$ | not added | 0 |
| 16 | 410 | (1) | 5/95 | " | Y(NO$_3$)$_3$ | not added | 0 |
| 17 | 320 | (1) | 6/94 | " | YCl$_3$ | clay | 3 |

16
Note:
(1) Zirconium oxide obtained by the thermal decomposition of zirconyl hydroxide
(3) Wt. % of sintering aid based on the total weight of ceramics

TABLE 2(a)-2

| No. | Thermal decomposition tem. × time (°C.) (hr.) | Firing, tem. × time (°C.) (hr.) | (4) $\frac{T(200) + C(200)}{T(200) + C(200) + M(11\bar{1})}$ | Average crystal grain size (μm) | Flexural strength (kg/mm$^2$) | Flexural strength after durability test (kg/mm$^2$) |
|---|---|---|---|---|---|---|
| 1 | not effected | 1,200° C. × 15 hr. | 0.98 | 0.3 | 98 | 90 |
| 2 | 800° C. × 5 hr. | 1,400° C. × 5 hr. | 0.91 | 0.8 | 96 | 87 |
| 3 | not effected | 1,200° C. × 5 hr. | 0.93 | 0.3 | 87 | 81 |
| 4 | 1,000° C. × 3 hr. | 1,400° C. × 5 hr. | 0.92 | 0.7 | 101 | 92 |
| 5 | not effected | 1,100° C. × 10 hr. | 0.89 | 0.2 | 75 | 75 |
| 6 | not effected | 1,200° C. × 10 hr. | 1.0 | 0.3 | 69 | 66 |
| 7 | 800° C. × 5 hr. | 1,300° C. × 5 hr. | 0.97 | 0.5 | 63 | 61 |
| 8 | 1,000° C. × 2 hr. | 1,400° C. × 5 hr. | 0.91 | 0.9 | 65 | 62 |
| 9 | 700° C. × 2 hr. | 1,400° C. × 2 hr. | 0.96 | 0.8 | 59 | 55 |
| 10 | 1,000° C. × 2 hr. | 1,500° C. × 1 hr. | 0.86 | 1.4 | 60 | 53 |
| 11 | 800° C. × 3 hr. | 1,020° C. × 20 hr. | 0.78 | 0.2 | 48 | 46 |
| 12 | 250° C. × 2 hr. | 1,250° C. × 5 hr. | 0.96 | 0.3 | 41 | 42 |
| 13 | 800° C. × 5 hr. | 1,120° C. × 10 hr. | 0.75 | 0.2 | 43 | 40 |
| 14 | 1,000° C. × 2 hr. | 1,380° C. × 5 hr. | 0.95 | 0.7 | 39 | 39 |
| 15 | not effected | 1,450° C. × 3 hr. | 0.76 | 1.0 | 45 | 41 |
| 16 | 1,200° C. × 1 hr. | 1,530° C. × 2 hr. | 0.72 | 1.8 | 47 | 39 |
| 17 | 900° C. × 3 hr. | 1,300° C. × 5 hr. | 0.91 | 0.4 | 37 | 35 |

Note:
(4) C(200): intensity of X-ray diffraction from the plane (200) of cubic phase
T(200): intensity of X-ray diffraction from the plane (200) of tetragonal phase
M(11$\bar{1}$): intensity of X-ray diffraction from the plane (11$\bar{1}$) of monoclinic phase

TABLE 2(b)-1

| No. | Crystallite size of zirconium oxide (Å) | | Molar ratio of stabilizer/ZrO$_2$ calculated as oxide | Kind of stabilizer indicated by oxide | Kind of stabilizer | Kind of sintering aid | (3) Addition amount of sintering acid (wt %) |
|---|---|---|---|---|---|---|---|
| 18 | 770 | | 6/94 | Y$_2$O$_3$ | YCl$_3$ | not added | 0 |
| 19 | 160 | | 7/93 | " | Y(NO$_3$)$_3$ | alumina | 3 |
| 20 | 440 | (1) | 7/93 | " | Y$_2$O$_3$ | clay | 10 |
| 21 | amorphous | | 4/96 | " | Y$_2$O$_3$ | not added | 0 |
| 22 | amorphous | (1) | 5/95 | " | Y(NO$_3$)$_3$ | alumina | 3 |
| 23 | 380 | (2) | 5/95 | " | YCl$_3$ | clay | 5 |
| 24 | 420 | | 1.5/98.5 | Y$_2$O$_3$ | Y$_2$O$_3$ | not added | 0 |
| 25 | 420 | | 8/92 | " | Y$_2$O$_3$ | not added | 0 |
| 26 | 1,080 | | 3/97 | " | YCl$_3$ | clay | 5 |
| 27 | 320 | | 5/95 | " | YCl$_3$ | " | 5 |

TABLE 2(b)-1-continued

| No. | Crystallite size of zirconium oxide (Å) | Molar ratio of stabilizer/ZrO$_2$ calculated as oxide | Kind of stabilizer indicated by oxide | Kind of stabilizer | Kind of sintering aid | (3) Addition amount of sintering acid (wt %) |
| --- | --- | --- | --- | --- | --- | --- |
| 28 | 450 | 5/95 | " | YCl$_3$ | " | 5 |

Note:
(1) Zirconium oxide obtained by the thermal decomposition of zirconyl hydroxide
(2) Zirconium oxide and yttrium oxide were mixed by coprecipitating them by adding ammonia to an aqueous solution containing zirconium chloride and yttrium chloride.
(3) Wt. % of sintering aid based on the total weight of ceramics

TABLE 2(b)-2

| No. | Thermal decomposition, tem. × time (°C.) (hr.) | Firing tem. × time (°C.) (hr.) | (4) $\frac{T(200) + C(200)}{T(200) + C(200) + M(11\bar{1})}$ | Average crystal grain size (μm) | Flexural strength (kg/mm$^2$) | Flexural strength after durability test (kg/mm$^2$) |
| --- | --- | --- | --- | --- | --- | --- |
| 18 | 1,200° C. × 1 hr. | 1,400° C. × 2 hr. | 0.88 | 0.5 | 38 | 37 |
| 19 | not effected | 1,250° C. × 5 hr. | 1.0 | 0.3 | 29 | 30 |
| 20 | 700° C. × 1 hr. | 1,020° C. × 20 hr. | 0.74 | 0.2 | 28 | 27 |
| 21 | not effected | 1,100° C. × 10 hr. | 0.95 | 0.2 | 71 | 73 |
| 22 | not effected | 1,200° C. × 5 hr. | 1.0 | 0.3 | 47 | 46 |
| 23 | 700° C. × 1 hr. | 1,250° C. × 5 hr. | 0.98 | 0.3 | 45 | 45 |
| 24 | not effected | 1,200° C. × 5 hr. | (M alone) | 0.3 | <1 | broken |
| 25 | not effected | 1,400° C. × 5 hr. | 1.0 (C alone) | 1.1 | 13 | 14 |
| 26 | 800° C. × 5 hr. | 1,300° C. × 5 hr. | 0.13 | 2.2 | 51 | broken |
| 27 | " | 900° C. × 15 hr. | 0.62 | 0.1 | 31 | broken |
| 28 | " | 1,600° C. × 2 hr. | 0.59 | 3.1 | 34 | broken |

Note:
(4) C(200): intensity of X-ray diffraction from the plane (200) of cubic phase
T(200): intensity of X-ray diffraction from the plane (200) of tetragonal phase
M(11$\bar{1}$): intensity of X-ray diffraction from the plane (11$\bar{1}$) of monoclinic phase It can be seen from Tables 1 and 2 that the zirconia ceramics according to the present invention have a very high strength, show very little deterioration of strength due to use for a long period of time and have a low volume resistivity.

As described above, the zirconia ceramics according to the present invention, which consist of crystal grains having a mixed phase consisting essentially of cubic phase and tetragonal phase or having a phase consisting essentially of tetragonal phase, which crystal grains have a particle size of not larger than 2 μm, have a very high strength, show very little deterioration of strength due to the lapse of time within the specifically limited temperature range of 200°–300° C. and are free from variation of dimensions due to heat treatment. Therefore, the zirconia ceramics of the present invention are advantageously used as industrial materials, which are required to have a high strength and a high thermal resistance, for example, as solid electrolyte for oxygen concentration cells, machine parts for internal combustion engines, thermistors, cutting tools and the like, and are very useful in industry.

What is claimed is:

1. Zirconia ceramics consisting essentially of ZrO$_2$ and Y$_2$O$_3$ in a molar ratio of Y$_2$O$_3$/ZrO$_2$ of 2/98 ~ 7/93, and consisting of crystal grains having a mixed phase consisting essentially of tetragonal phase and cubic phase or having a phase consisting essentially of tetragonal phase, the average size of said crystal grains being not larger than 2 μm.

2. Zirconia ceramics according to claim 1, wherein the molar ratio of Y$_2$O$_3$/ZrO$_2$ is within the range of 2/98 ~ 4/96 and the crystal grains have a phase consisting essentially of tetragonal phase.

3. A method of producing zirconia ceramics consisting of crystal grains having a mixed phase consisting essentially of tetragonal phase and cubic phase or having a phase consisting essentially of tetragonal phase, said crystal grains having an average grain size of not larger than 2 μm, wherein a mixture of zirconium oxide and an yttrium compound in a molar ratio, calculated as oxide, of Y$_2$O$_3$/ZrO$_2$ of 2/98 ~ 7/93 is molded into a molded article, and the molded article is fired at a temperature within the range of 1,000° ~ 1,550° C., wherein said zirconium oxide has a crystallite size of not larger than 700 Å.

4. A method according to claim 3 wherein the zirconium oxide having a crystallite size of not larger than 700 Å is produced by thermal decomposition of zirconyl hydroxide at a temperature within the range of 200° ~ 1,100° C.

5. A method of producing zirconia ceramics consisting of crystal grains having a mixed phase consisting essentially of tetragonal phase and cubic phase or having a phase consisting essentially of tetragonal phase, said crystal grains having an average grain size of not larger than 2 μm, wherein a mixture of zirconium oxide and an yttrium compound in a molar ratio, calculated as oxides, of Y$_2$O$_3$/ZrO$_2$ of 2/98 ~ 7/93 is molded into a molded article, and the molded article is fired at a temperature within the range of 1,000° ~ 1,500° C., wherein said zirconium oxide is amorphous.

6. A method according to claim 5, wherein the amorphous zirconium oxide is produced by thermal decomposition of zirconyl hydroxide at a temperature within the range of 200° ~ 1,100° C.

* * * * *